US009860455B2

(12) United States Patent
Umezawa

(10) Patent No.: US 9,860,455 B2
(45) Date of Patent: Jan. 2, 2018

(54) OBJECT INFORMATION ACQUIRING APPARATUS AND SIGNAL PROCESSING METHOD

(71) Applicant: CANON KABUSHIKI KAISHA, Tokyo (JP)

(72) Inventor: Kohtaro Umezawa, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 253 days.

(21) Appl. No.: 14/629,645

(22) Filed: Feb. 24, 2015

(65) Prior Publication Data

US 2015/0256761 A1  Sep. 10, 2015

(30) Foreign Application Priority Data

Mar. 10, 2014 (JP) .................. 2014-046388

(51) Int. Cl.
  *G06K 9/00* (2006.01)
  *H04N 5/243* (2006.01)
  (Continued)

(52) U.S. Cl.
  CPC ............ *H04N 5/243* (2013.01); *A61B 5/0095* (2013.01); *A61B 8/0825* (2013.01); *A61B 8/14* (2013.01);
  (Continued)

(58) Field of Classification Search
  CPC ....... A61B 5/0095; A61B 8/0825; A61B 8/14; A61B 8/5207; A61B 8/5269; H04N 5/2351; H04N 5/243
  See application file for complete search history.

(56) References Cited

U.S. PATENT DOCUMENTS 8,489,176 B1 *  7/2013  Ben-David .......... A61B 6/4258
                                                 600/3
8,670,040 B2 *  3/2014  Nokita ................... G06T 5/003
                                                 348/222.1
(Continued)

FOREIGN PATENT DOCUMENTS

JP   2008-307372   12/2008

OTHER PUBLICATIONS

Chunming et al (Level Set Method for Image Segmentation in the Presence of Intensity Inhomogeneities With Application to MRI, IEEE Transactions on Image Processing, vol. 20, No. 7, pp. 2007-2016, Jul. 2011.*

(Continued)

*Primary Examiner* — Amara Abdi
(74) *Attorney, Agent, or Firm* — Fitzpatrick, Cella, Harper & Scinto

(57) ABSTRACT

An object information acquiring apparatus comprising: a receiver configured to receive an acoustic wave propagating from an object; a distribution acquiring unit configured to acquire a distribution of object information by acquiring pieces of object information relative to respective positions in an object from a received acoustic wave; a resolution information acquiring unit configured to acquire a distribution of resolution information that is based on pieces of resolution information of object information relative to each of the positions; and an intensity correction processor configured to correct an intensity of each piece of object information included in a distribution of object information on the basis of a distribution of resolution information.

18 Claims, 11 Drawing Sheets

(51) Int. Cl.
*A61B 8/14* (2006.01)
*A61B 8/08* (2006.01)
*A61B 5/00* (2006.01)
*H04N 5/235* (2006.01)

(52) U.S. Cl.
CPC .......... *A61B 8/5207* (2013.01); *A61B 8/5269* (2013.01); *H04N 5/2351* (2013.01)

(56) References Cited

U.S. PATENT DOCUMENTS

| | | | | |
|---|---|---|---|---|
| 2009/0002685 A1* | 1/2009 | Fukutani | ............. | A61B 5/0073 356/72 |
| 2010/0174197 A1* | 7/2010 | Nakajima | ............. | A61B 5/0084 600/478 |
| 2010/0191109 A1* | 7/2010 | Fukutani | ............. | A61B 5/0059 600/437 |
| 2012/0183190 A1* | 7/2012 | Fukutani | ............. | A61B 5/0073 382/128 |
| 2013/0148872 A1* | 6/2013 | Aisaka | ............. | A61B 3/12 382/128 |
| 2013/0336088 A1* | 12/2013 | Umezawa | ............. | A61B 5/0095 367/8 |
| 2014/0249402 A1* | 9/2014 | Kimchy | ............. | A61B 5/055 600/411 |
| 2014/0316236 A1* | 10/2014 | Umezawa | ............. | A61B 5/1128 600/407 |

OTHER PUBLICATIONS

C. Li et al., "A Level Set Method for Image Segmentation in the Presence of Intensity Inhomogeneities with Application to MRI", *IEEE Transactions on Image Processing*, Jul. 2011, vol. 20, No. 7, pp. 2007-2016.

* cited by examiner

OBJECT INFORMATION ACQUIRING APPARATUS AND SIGNAL PROCESSING METHOD

BACKGROUND OF THE INVENTION

Field of the Invention

The present invention relates to an object information acquiring apparatus and a signal processing method.

Description of the Related Art

A bio-information imaging apparatus 500 proposed in Japanese Patent Application Laid-open No. 2008-307372 has a light source 511, an acoustic-wave detector 513, a photodetector 514, and a calculation unit 522. The light source 511 irradiates a living body with light. The acoustic-wave detector 513 detects an acoustic wave generated by a light absorber 519 in the living body having absorbed a portion of the energy of light delivered from the light source 511 to the living body, and converts the acoustic wave, which is generated by a light absorbing body, into a first electric signal. The photodetector 514 detects the light intensity of a portion of the light delivered from the light source 511 to the living body which propagates through the living body, and converts the light intensity into a second electric signal. The calculation unit 522 utilizes the result of analysis of one of the first and second electric signals to analyze the other electric signal, to calculate an optical-characteristic value distribution information on the living body. The absorption coefficient distribution of blood vessels in the living body is determined on the basis of the calculation result.

An MRI that is an image diagnosis apparatus is proposed in Chunming Li, Rui Huang, Zhaohu a Ding, J. Chris Gatenby, Dimitris N. Metaxas, and John C. Gore, "A Level Set Method for Image Segmentation in the Presence of Intensity Inhomogeneities With Application to MRI," IEEE Transactions on Image Processing, vol. 20, no. 7, pp. 2007-2016, July 2011. This apparatus adopts a correction method for appropriately extracting the shapes of blood vessels. That is, a resultant change in the global intensity of an original image is calculated to obtain a bias value, which is then used to perform correction to make the intensity of the image even. Subsequently, a level set method is used to extract blood vessels. At this time, the bias value is calculated using a convolution of the original image and a Gaussian function.

Patent Literature 1: Japanese Patent Application Laid-open No. 2008-307372

Non Patent Literature 1: Chunming Li, Rui Huang, Zhaohu a Ding, J. Chris Gatenby, Dimitris N. Metaxas, and John C. Gore, "A Level Set Method for Image Segmentation in the Presence of Intensity Inhomogeneities With Application to MRI," IEEE Transactions on Image Processing, vol. 20, no. 7, pp. 2007-2016, July 2011.

SUMMARY OF THE INVENTION

Japanese Patent Application Laid-open No. 2008-307372 utilizes data obtained through photoacoustic imaging and diffuse light imaging to increase the resolution of object information and to reduce calculation time. However, Japanese Patent Application Laid-open No. 2008-307372 does not correct the intensity of the optical-characteristic value distribution information obtained. Furthermore, according to Chunming Li, Rui Huang, Zhaohu a Ding, J. Chris Gatenby, Dimitris N. Metaxas, and John C. Gore, "A Level Set Method for Image Segmentation in the Presence of Intensity Inhomogeneities With Application to MRI," IEEE Transactions on Image Processing, vol. 20, no. 7, pp. 2007-2016, July 2011, the intensity of the image obtained is corrected. However, a variation (a distribution) in resolution information relative to the object position due to the apparatus is not taken into account, and thus, even though the intensity of the object information is corrected, the intensity is made uneven by the variation in resolution information.

With the foregoing in view, it is an object of the present invention to provide an object information acquiring apparatus that can correct the intensity of object information relative to each position in the object on the basis of the resolution for each position in the object due to the object information acquiring apparatus.

To accomplish the object, an aspect of the present invention provides an object information acquiring apparatus comprising: a receiver configured to receive an acoustic wave propagating from an object; a distribution acquiring unit configured to acquire a distribution of object information by acquiring pieces of object information relative to respective positions in the object from the received acoustic wave; a resolution information acquiring unit configured to acquire a distribution of resolution information that is based on pieces of resolution information of object information relative to each of the positions; and an intensity correction processor configured to correct an intensity of each piece of object information included in the distribution of object information on the basis of the distribution of the resolution information.

An aspect of the present invention also provides an object information acquiring apparatus comprising: a receiver configured to receive an acoustic wave propagated from an object; a distribution acquiring unit configured to acquire, from the received acoustic wave, a first piece of object information relative to a first position in the object and a second piece of object information relative to a second position, which is different from the first position; a resolution information acquiring unit configured to acquire a first piece of resolution information corresponding to the first position and a second piece of resolution information corresponding to the second position and having a value different from a value of the first piece of resolution information; and an intensity correction processor configured to correct an intensity of the first piece of object information on the basis of the first piece of resolution information acquired, and correct an intensity of the second piece of object information on the basis of the second piece of resolution information acquired.

An aspect of the present invention also provides a signal processing method comprising: acquiring a distribution of resolution information that is based on pieces of resolution information of object information that depend on each position in an object; and correcting an intensity of each piece of object information relative to a corresponding one of positions in the object on the basis of the distribution of the resolution information.

The aspects of the present invention can provide an object information acquiring apparatus that can correct the intensity of object information relative to each position in the object on the basis of the resolution for each position in the object due to the object information acquiring apparatus.

Further features of the present invention will become apparent from the following description of exemplary embodiments with reference to the attached drawings.

DESCRIPTION OF THE EMBODIMENTS

Figure 1:
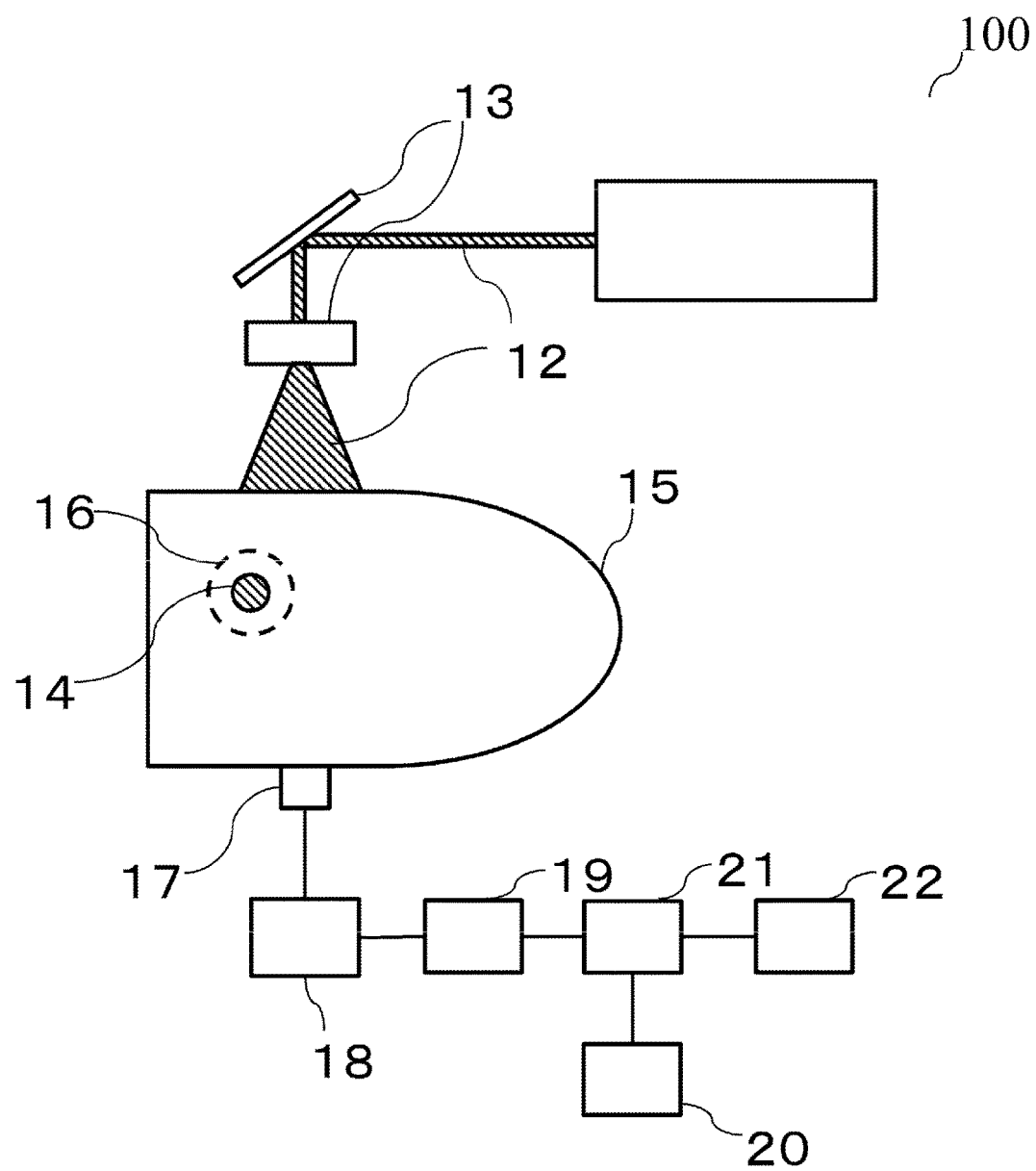
FIG. 1 is a block diagram depicting Embodiment 1 of an object information acquiring apparatus according to the present invention.

Embodiments of the present invention will be described below in detail with reference to the drawings. The same components are in principle denoted by the same reference numerals and will not be described below. However, detailed calculating formulae, calculation procedures, and the like should be appropriately changed depending on the configuration of an apparatus to which the invention is applied and various conditions and are not intended to limit the scope of the present invention to the description below.

An acoustic-wave acquiring apparatus that is an object information acquiring apparatus according to the present invention includes an apparatus utilizing an ultrasonic echo technique and configured to transmit an ultrasonic wave to an object and to receive a reflected wave (echo wave) reflected inside the object to acquire object information as image data. Furthermore, the acoustic-wave acquiring apparatus includes an apparatus utilizing a photoacoustic effect and configured to irradiates the object with light (electromagnetic wave) and to receive an acoustic wave generated inside the object to acquire object information as image data.

For the former apparatus utilizing the ultrasonic echo technique, the object information acquired is information reflecting differences in acoustic impedance among tissues inside the object. For the latter apparatus utilizing the photoacoustic effect, the object information acquired indicates the distribution of sources of acoustic waves resulting from light irradiation, the distribution of initial pressures in the object, or the distribution of light energy absorption densities and the distribution of absorption coefficients which are derived from the distribution of initial sound pressures, or the distribution of concentrations of substances providing the tissue. The distribution of concentrations of substances is, for example, the distribution of oxygen saturations or the distribution of concentrations of oxidized and reduced hemoglobin.

The acoustic wave as used herein is typically an ultrasonic wave and includes an elastic wave referred to as a sound wave, an ultrasonic wave, or an acoustic wave. An acoustic wave generated by a photoacoustic effect is referred to as a photoacoustic wave or a photoacoustic wave. A photodetector (for example, a probe) receives an acoustic wave generated or reflected inside the object.

Embodiment 1

(Basic Configuration)

FIG. 1 is a block diagram depicting Embodiment 1 of an object information acquiring apparatus 100 (hereinafter simply referred to as an "apparatus 100") according to an embodiment of the present invention.

The apparatus 100 according to Embodiment 1 is an apparatus that irradiates an object 15 with pulsed light 12 and receives and analyzes a photoacoustic wave 16, which is generated inside an object due to the pulsed light 12, to image the distribution of object information. The distribution of object information is generally the distribution of initial pressures, the distribution of light absorption energy densities, the distribution of absorption coefficients, or the distribution of concentrations of substances providing the tissue. Subject information is elements forming the distribution of object information. For example, the distribution of absorption coefficients is formed by using absorption coefficients as elements. In the present embodiment, the distribution of object information is specifically assumed to be the distribution of absorption coefficients.

In the apparatus 100, the measured distribution of object information may suffer intensity unevenness due to apparatus factors such as the directionality of a probe 17. Thus, in Embodiment 1, the intensity unevenness in the distribution of absorption coefficients is corrected taking into account variations in resolution for each position in a measurement area for the apparatus 100.

A configuration of the apparatus 100 according to Embodiment 1 will be described with reference to FIG. 1. A photoacoustic measurement apparatus according to Embodiment 1 has a light source 11, an optical system 13, a probe 17, a signal processor 18, a data processor 19, a resolution information acquiring unit 20, an intensity correction processor 21, and a display 22. A light irradiator includes the light source 11 and the optical system 13. A receiver includes the probe 17. A distribution acquiring unit includes the signal processor 18 and the data processor 19.

The pulsed light 12 emitted by the light source 11 is delivered to the object 15 via the optical system 13. When a portion of the energy of light having propagated through the object is absorbed by a light absorber 14 such as blood, the light absorber 14 generates an acoustic wave 16 as a result of thermal expansion. The acoustic wave 16 generated inside the object is received by the probe 17 and analyzed by the signal processor 18 and the data processor 19 to form pieces of object information into the distribution of object information.

Furthermore, the apparatus 100 according to the present embodiment acquires resolution information relative to a position in the object 15 from the resolution information acquiring unit 20. Based on the resolution information acquired, the intensity correction processor 21 corrects the intensity of each piece of the object information. That is, in this case, the intensity of each of the absorption coefficients included in the distribution of absorption coefficients is corrected. A corrected distribution of absorption coefficients is formed from corrected absorption coefficients and output through the display 22.

The configuration of the apparatus 100 according to the present embodiment will be described below.

<<Light Source 11>>

The light source 11 is an apparatus that generates pulsed light 12 delivered to the object 15. The light source 11 is desirably a laser light source configured to provide a high output, but may be a light emitting diode, a flash lamp, or the like. When a laser is used as the light source 11, various lasers such as a solid laser, a gas laser, a dye laser, and a semiconductor laser may be used. Irradiation timings, waveform, intensity, and the like are controlled by a light source controller, which is not shown in figures. The light source controller may be provided separately from the light source 11 or integrated with the light source 11.

Furthermore, to allow the acoustic wave 16 to be effectively generated, light needs to be delivered in a sufficiently short time in accordance with the heat characteristics of the object 15. When the object 15 is a living body, the pulsed light 12 generated by the light source 11 suitably has a pulse width of approximately 10 to 100 nanoseconds. Additionally, the pulsed light 12 desirably has a wavelength appropriate to allow light to propagate through to the interior of the object 15. Specifically, if the object 15 is a living body, the wavelength is desirably at least 500 nm and at most 1,200 nm. Moreover, the pulsed light 12 desirably has a wavelength that increases the absorption coefficient for the light absorber 14, which is an observation target. The light source 11 can desirably deliver laser light with several types of wavelengths.

<<Optical System 13>>

The optical system 13 is means for guiding the pulsed light 12 generated by the light source 11 to the object 15. The optical system 13 is formed using a mirror that reflects light, a lens that condenses or enlarges light or changes the shape of light, a diffuser that diffuses light, or the like. These optical members may be used to set irradiation conditions such as the irradiation shape of the pulsed light 12, a light density, and an irradiation direction with respect to the object 15, to any values. Light is preferably spread so as to have a certain area rather than being condensed by a lens so that safety for the object 15 can be improved and a diagnosis area can be increased.

<<Subject 15 and Light Absorber 14>>

The object 15 and the light absorber 14, which are not components of the present invention, will be described below. The object 15 is a target for photoacoustic measurement and is, for example, the breast, finger, hand, or foot of a human body or an animal. In this case, the human breast is the object 15.

The apparatus 100 according to the present embodiment can image the light absorber 14 which is present in the object 15 and which has a relatively large light absorption coefficient. When the object 15 is a living body, the light absorber 14 is specifically water, lipid, melanin, collagen, protein, oxygenated hemoglobin, reduced hemoglobin, or the like. Alternatively, the light absorber 14 is a blood vessel containing a large amount of oxygenated or reduced hemoglobin, a malignant tumor containing a large amount of new blood vessels, or the like. By imaging the light absorber 14, the object information acquiring apparatus according to the present embodiment allows imaging of the blood vessel, diagnosis of a malignant tumor of humans or animals, a blood vessel disease, or the like, follow-up of chemical treatment, or the like.

<<Probe 17>>

The probe 17 is means for receiving the acoustic wave 16 generated inside the object 15 in connection with the pulsed light 12 delivered to the object 15 to convert the acoustic wave 16 into an analog electric signal. The acoustic wave 16 according to the present invention is typically an ultrasonic wave and includes an elastic wave referred to as a sound wave, an ultrasonic wave, or a photoacoustic wave. The probe 17 receives these elastic waves generated inside the object.

The probe 17 is referred to as a transducer. The probe 17 may be a single acoustic detector or include a plurality of acoustic detectors. Furthermore, the probe 17 may be a plurality of reception elements arranged in a one- or two-dimensional manner. The use of multidimensional array elements allows an acoustic wave to be simultaneously received at a plurality of locations, thus enabling a reduction in measurement time and in the adverse effect of vibration of the object 15 or the like.

Furthermore, the probe 17 desirably has a high sensitivity and a wide frequency band. Specifically, examples of the probe 17 include probes using piezoelectric ceramics (PZT), polyvinylidene fluoride resin (PVDF), capacitive micromachine ultrasonic transducers (CMUT), or a Fabry-Perot interferometer. However, the probe 17 is not limited to the probes listed above but may be any probe as long as the probe can provide the functions of a probe.

<<Signal Processing Section 18>>

The signal processor 18 is means for amplifying and converting the analog electric signal obtained from the probe 17 into a digital signal. The signal processor 18 includes an amplifier, an A/D converter, and a field programmable gate array (FPGA) chip. When a plurality of detection signals is obtained from the probe 17, the signal processor 18 can desirably process the plurality of signals at the same time.

<<Data Processing Section 19>>

The data processor 19 is means for processing the digital signal obtained by the signal processor 18 to generate image data. That is, the data processor 19 is means for performing image reconstruction. Examples of the data reconstruction method executed by the data processor 19 include Fourier transform, universal back-projection, filtered back-projection, and a sequential reconstruction, and any image reconstruction method may be used. Furthermore, the signal processor 18 and the data processor 19 may be separately provided or integrated together.

<<Resolution Information Acquisition Section 20>>

The resolution information acquiring unit 20 is means for acquiring resolution information when the apparatus 100 measures the object 15. The resolution information is the capability of the apparatus 100 for data measurement. The resolution information is desirably the half width at half maximum of a point spread function (PSF) indicative of the extent of spread from a spot source of a unit system in the apparatus 100. However, the resolution information is not limited to this information but may be any indicator such as an impulse response, the full width at half maximum of an LSF (Line Spread Function), a spatial resolution, or the sharpness of an image which represents the degree of blurriness of the image of the apparatus 100.

Furthermore, the resolution information is desirably the two- or three-dimensional spatial distribution of the resolution information on the apparatus. However, the resolution information is not limited to such a distribution but may be resolution information relative to any one point in the data or resolution information relative to any plurality of points in the data. Alternatively, the resolution information may be the three-dimensional spatial distribution of resolution information calculated using the resolution information relative to the one or plurality of points.

The resolution information may be pre-input to the resolution information acquiring unit 20, input to the resolution information acquiring unit 20 by an operator, or automatically acquired by the resolution information acquiring unit 20 using simulation or phantom measurement. When the operator inputs resolution information to the resolution information acquiring unit 20, the resolution information acquiring unit 20 is input means such as a keyboard and memory that holds inputs. The resolution information may be saved to memory in the FPGA in the signal processor 18. In that case, the resolution information acquiring unit 20 is a memory manager that allows the resolution information to be acquired from the memory. When the apparatus 100 calculates the resolution information using simulation, the resolution information acquiring unit 20 is a processor that allows calculations to be executed. When the resolution information is acquired by allowing the apparatus 100 to automatically measure a phantom or the like or manually operating the apparatus 100 to perform the measurement, the information acquiring unit 20 receives acquisition results.

A method for calculating the resolution information may be such that the operator performs photoacoustic measurement on a phantom containing wires and cysts shaped like spheres or the like, and at a certain point, calculates the resolution information for each direction. Alternatively, the resolution information relative to each position in the object 15 may be calculated by complementing discrete resolution information calculated for each of the portions of the distribution corresponding to the plurality of cysts. Alternatively, the apparatus 100 may calculate the resolution information relative to each position in the object 15 using simulation or in an analyzing manner.

The "certain point" refers to a point inside the distribution of absorption coefficients for which the resolution information can be calculated. In the present technique, the resolution information for the X, Y, and Z directions at any one point inside a measurement area for the apparatus 100 is assumed to be the resolution information for the X, Y, and Z directions which is referenced for correction of the intensity of the distribution of absorption coefficients.

The resolution information is calculated, for example, for internal portions of the measured distribution of absorption coefficients corresponding to areas where the cysts are present, based on a difference between an imaged cyst diameter and an original cyst diameter. In this case, the root mean squared error between the imaged cyst diameter and the original cyst diameter is used for the calculation. The calculated resolution is used as the resolution information for the X, Y, and Z directions at the "point" where the cyst is present. Alternatively, the resolution information for one portion of the distribution corresponding to the point where the cyst is present may be used as the resolution information for the apparatus 100. The "point" for which the resolution information of the apparatus 100 is calculated as described above is expressed as the "certain point". In the present embodiment, the resolution information is calculated using image information relative to a particular point on an image. However, any other method may be used to calculate the resolution information.

In the method for calculating the resolution information using a phantom, first, the cross unit of the cyst in a phantom image obtained by the apparatus 100 is imaged. Subsequently, the intensity distribution of the cyst in the cross-unital direction is fitted using a Gaussian function or the like.

Then, the difference between the square of the full width at half maximum of the cyst and the square of the full width at half maximum at a portion of the distribution corresponding to the half of the maximum value of the Gaussian function is calculated. Then, the root square of the value obtained is determined. This is a method of calculating the full width at half maximum in a particular direction of the PSF. Alternatively, for example, the half width at half maximum of the fitted function may be determined. The resolution information may be calculated manually by the operator or automatically by the apparatus 100.

<<Intensity Correction Processing Section 21>>

The intensity correction processor 21 is means for loading the resolution information acquired by the resolution information acquiring unit 20 and correcting values in the object information such as the absorption coefficient.

(Method for Correcting Intensity)

A method for correcting the intensity will be described below. First, the distribution of absorption coefficients is formed, which is the distribution of object information that is based on absorption coefficients, which are object information. An intensity trend distribution is calculated from the distribution of absorption coefficients. The intensity trend distribution is an uneven measured distribution of sound pressures or absorption coefficients resulting from the directionality of the probe or the unevenness of applied magnetic fields, or an intensity distribution indicating uneven global changes on an MRI image. The intensity trend distribution is desirably calculated by blurring the values in the object information. The blurring is used to calculate global changes in the values which are not affected by local changes in the values. The method is not limited to the present technique but any method may be used as long as the method allows calculation of the intensity trend distribution of the distribution of object information. The present technique is different from the conventional technique in that the resolution information dependent on the configuration of the apparatus 100 is used in calculating the intensity trend distribution.

For the blurring, a moving average process in a three-dimensional direction or a three-dimensional convolution with a three-dimensional Gaussian function is desirably performed. The technique used herein assumes a convolution of the distribution of absorption coefficients and the three-dimensional Gaussian function. The convolution is a mathematical process between two functions, f and g, illustrated in Equation (1) and is a binary operation in which the function g is overlapped on and added to the function f being translated.

[Math. 1]

$$(f*g)(t) = \int f(\tau)g(t-\tau)d\tau \qquad \text{Equation 1}$$

An integral interval is denoted by $\tau$, and a variable of the function g is denoted by t. In general, the function g is referred to as a convolution kernel. In the convolution in image processing, the convolution kernel g is convoluted with the image data f. In the present embodiment, the distribution of absorption coefficients (F) is used as the function f, and the function g is a Gauss kernel that is a convolution kernel. That is, the function g is a convolution kernel using a three-dimensional Gaussian function (G) illustrated in Equation 2. The reason why the three-dimensional Gaussian function is used as the convolution kernel is that the Gaussian function is generally used as a model for the PSF. Hence, when the model for the PSF does not use the three-dimensional Gaussian function, a function complying with the model may be used.

[Math. 2]

$$G(X, Y, Z) = \frac{1}{2\pi\sigma_X\sigma_Y\sigma_Z}\exp\left[-\left(\frac{X^2}{2\sigma_X^2} + \frac{Y^2}{2\sigma_Y^2} + \frac{Z^2}{2\sigma_Z^2}\right)\right] \quad \text{Equation 2}$$

In Equation 2, the variances of the Gaussian function in the X direction, the Y direction, and the Z direction are denoted by σX, σY, and σZ, respectively. The relation between the variance σ of the three-dimensional Gaussian function and the three-dimensional PSF is expressed by:

[Math. 3]

$$\text{PSF}(i)=2\sigma i\sqrt{2\ln 2}\,(i=X,Y,Z) \quad \text{Equation 3}$$

where the PSF for the X direction at an observation point is denoted by PSF(X). Then, the variance σ used for the Gaussian function is obtained from the calculated PSF. Equation 4 indicative of the convolution in the present embodiment is obtained from Equation 1 and Equation 2.

[Math. 4]

$$F*G(X, Y, Z) = \int \frac{1}{2\pi\sigma_X\sigma_Y\sigma_Z}F(x, y, z)$$
$$\exp\left[-\left(\frac{(X-x)^2}{2\sigma_X^2} + \frac{(Y-y)^2}{2\sigma_Y^2} + \frac{(Z-z)^2}{2\sigma_Z^2}\right)\right]d\tau \quad \text{Equation 4}$$

In this regard, dτ=dxdydz. The distribution of absorption coefficients (F) is three-dimensional voxel data for a finite area. Desirably, the Gaussian function (G) is similarly three-dimensional voxel data for a finite area. Hence, rewriting Equation 3 to a convolution sum using discrete values results in Equation 5.

[Math. 5]

$$F*G(X, Y, Z) = \Sigma_{x,y,z}\frac{1}{2\pi\sigma_X\sigma_Y\sigma_Z}F(x, y, z)$$
$$\exp\left[-\left(\frac{(X-x)^2}{2\sigma_X^2} + \frac{(Y-y)^2}{2\sigma_Y^2} + \frac{(Z-z)^2}{2\sigma_Z^2}\right)\right] \quad \text{Equation 5}$$

In this regard, 99.73% of the Gaussian distribution is contained in ±3σ. Thus, the convolution is facilitated by setting the convolution kernel to be a finite rectangular parallelepiped area of 6σ on a side. It is assumed that the Gaussian function is located in the center of the rectangular parallelepiped area. In this case, the length of the convolution kernel is σ*6 on a side in the relevant direction. However, the size may be changed as long as the relative ratio of the resolution information for the X, Y, and Z directions is maintained. The voxel is assumed to be 0.25 mm on a side.

When, in the convolution in Equation 5, the functions F and G are executed as periodical functions, the value of F*G in the result of the convolution may vary in a boundary area. In that case, the function F, that is, the convolution is desirably performed after complementing the periphery of voxel data in the three-dimensional distribution of object information with data for a length equal to half of a side of the convolution kernel. This allows the convolution to be achieved without being affected by the value of the opposite boundary. At this time, the value of the complemented data is desirably zero but may be the value of data on the outermost periphery of the original distribution of object information. Alternatively, the convolution may be performed by using only signals inside the object area with respect to the measurement area or the convolution data may be weighted taking the number of data convolutions into account.

As described above, the convolution of the three-dimensional distribution of absorption coefficients and the three-dimensional convolution kernel allows the intensity trend distribution of the distribution of absorption coefficients to be calculated as three-dimensional voxel data. The intensity trend distribution is three-dimensional voxel data with the same size as that of the distribution of absorption coefficients.

When the resolution information input to the resolution information acquiring unit 20 is resolution information for each direction, in this case, each of the X, Y, and Z directions, at the certain point, the convolution kernel is determined in accordance with the resolution information. When the resolution information is resolution information changing in a certain direction, the size of the convolution kernel changes with respect to the direction. When the distribution of resolution information changes in each data area, the size of the convolution kernel is determined to vary depending on the position in the data area.

In this regard, the distribution of resolution information is a set of n (n is an integer of 2 or more) pieces of resolution information. For the distribution of resolution information, the n pieces of resolution information may all have the same value. Furthermore, when at least one of the n pieces of resolution information has a value different from the values of the other pieces of resolution information, the distribution of resolution information including the n pieces of resolution information is specifically referred to as resolution variation information. In other words, when the distribution of resolution information is a set of at least two pieces of resolution information and one of the two pieces of resolution information is different from the other piece of resolution information, the distribution of resolution information may specifically be referred to as resolution variation information.

In the present embodiment, the resolution information for the apparatus 100 is anisotropic, and the intensity of the distribution of absorption coefficients is corrected using the full width at half maximum of the PSF at a certain point as resolution information. In this case, the full width at half maximum of the PSF at the one point in the X direction and in the Y direction is 2 mm. The full width at half maximum of the PSF in the X direction and the Y direction is 1 mm. The resultant σ is multiplied by a constant, σX and σY are each 20 voxels, and σZ is 10 voxels. A scale factor for σ is empirically obtained. The length of the rectangular parallelepiped of the convolution kernel on a side is equal to 121 voxels, that is, 6σ plus 1, in the X and Y directions and to 61 voxels in the Z direction because the Gaussian function is located in the center of the kernel.

Then, an offset value is added to the entire intensity trend distribution of the distribution of absorption coefficients. Addition of the offset allows zero division of values to be prevented in a division process described below. In this case, substitution of the maximum value of the distribution of absorption coefficients is performed for an empirical reason. The intensity trend distribution with the offset value addition is similarly referred to as an intensity trend distribution.

The distribution of absorption coefficients with the intensity corrected can be calculated by executing a division process on the distribution of absorption coefficients calculated by the data processor 19 using the intensity trend distribution. For the correction of the intensity of the distribution of absorption coefficients, apart of the distribution of absorption coefficients is desirably extracted and corrected. However, the entire distribution of absorption coefficients may be corrected.

The absolute value of the corrected distribution of absorption coefficients has changed compared to the absolute value of the distribution of absorption coefficients calculated by the data processor 19. This is because the distribution of absorption coefficients has been divided by the intensity trend distribution. The absolute value of the corrected distribution of absorption coefficients changes depending on the value of the intensity trend distribution. To suppress the change, a constant value is added to the corrected distribution of absorption coefficients to allow the value of the corrected distribution to be made close to the value of the original distribution of absorption coefficients. Thus, the display 22 or the like can display the distribution as data with an intensity range close to the uncorrected intensity range.

The constant value for addition is desirably the ratio between the absolute value of the distribution of absorption coefficients and the maximum value of the uncorrected distribution of absorption coefficients or the ratio between the mean value of the corrected distribution of absorption coefficients and the mean value of the uncorrected distribution of absorption coefficients. However, instead of using this method, it is also preferable to newly display the corrected distribution of absorption coefficients within an intensity range different from the intensity range of the uncorrected distribution of absorption coefficients, for example, by means of normalization with the maximum value of the corrected distribution of absorption coefficients.

The display 22 is an apparatus that displays image data on the distribution of absorption coefficients generated by the intensity correction processor 21. Typically, a liquid crystal display or the like is utilized as the display 22. The display 22 need not necessarily be included in the apparatus 100 but may be provided outside the apparatus 100.

Flow of the Process According to Embodiment 1

Figure 2:
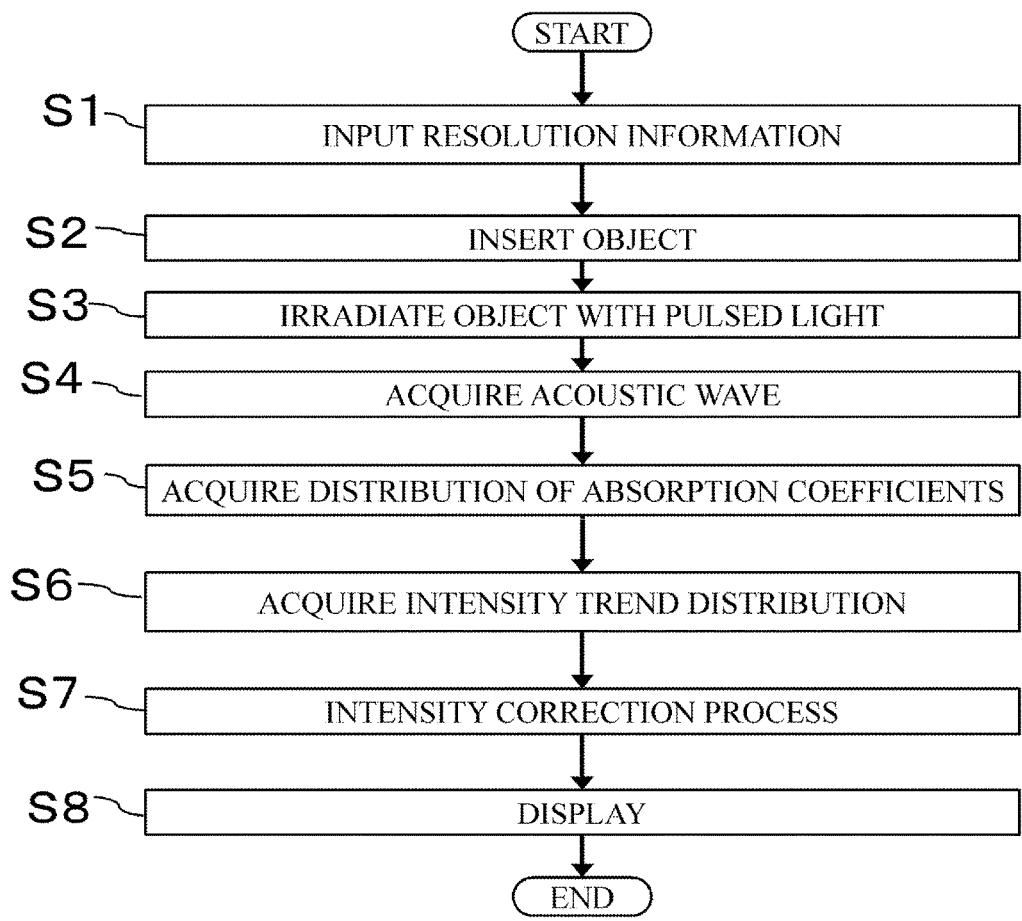
FIG. 2 is a flowchart depicting functions of the object information acquiring apparatus according to Embodiment 1.

FIG. 2 is a flowchart depicting the functions of the apparatus 100 according to Embodiment 1 of the present invention. Steps in FIG. 2 corresponding to components in FIG. 1 are denoted by the same reference numerals and will not be described unless otherwise needed. Before the flow is started, a phantom is measured, the resolution information for each direction in the apparatus 100 is calculated, and an offset is input to the apparatus 100.

In step S1, the resolution information is input to the resolution information acquiring unit 20. In step S2, the living body such as the breast, which is the object 15, is inserted into the apparatus 100. In step S3, the object 15 is irradiated with pulsed laser light with a single wavelength of 797 nm. In step S4, photoacoustic measurement is performed to allow the probe 17 to acquire the acoustic wave 16 propagating through the object 15. The probe 17 converts the acoustic wave 16 into an electric signal by a piezoelectric effect and inputs the electric signal to the signal processor 18. In step S5, the signal processor 18 converts the analog electric signal input to the signal processor 18 into a digital signal, and inputs the digital signal to the data processor 19. The data processor 19 calculates the distribution of absorption coefficients for the object 15 from the digital signal.

The Gaussian function generated in accordance with the resolution information input in step S6 is used to blur the absorption coefficients and thus the distribution of absorption coefficients. The offset is added to the blurred distribution of absorption coefficients to obtain an intensity trend distribution. In step S7, the original distribution of absorption coefficients is divided by the resultant intensity trend distribution to correct the distribution of absorption coefficients. In step S8, the distribution is displayed in accordance with the corrected distribution of absorption coefficients.

According to Embodiment 1, the apparatus 100 displays an image based on the distribution of absorption coefficients using the acoustic wave 16 propagating through the object 15, and can correct the intensity unevenness of the calculated distribution of absorption coefficients which is specific to the apparatus 100 to generate an image with a distribution of absorption coefficients providing visually even brightness.

Simulation of Embodiment 1

Figure 3A:
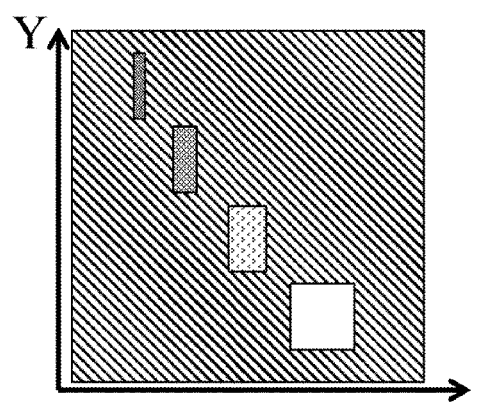
FIGS. 3A to 3C are diagrams depicting the distributions of absorption coefficients obtained before and after correction of intensity, in Embodiment 1.
Figure 3B:
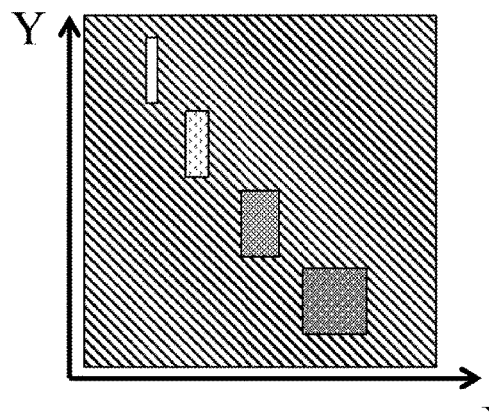
Figure 3C:
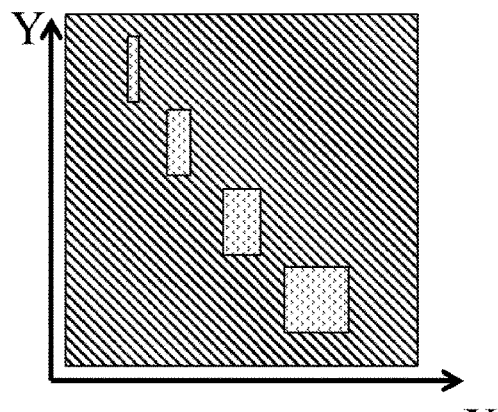

FIG. 3A to 3C are images depicting the results of verification based on simulation using the technique according to Embodiment 1. FIG. 3B and FIG. 3C are the same in image display range. FIG. 3A depicts data with the resolution varying depending on the location, as the distribution of object information.

FIG. 3A depicts a model in which four cysts are contained in a space. The resolution decreases in a positive direction on an X axis from the uppermost cyst to the lowermost cyst in the image. The intensity increases with decreasing resolution.

FIG. 3B is an image obtained using a conventional intensity correction method. The magnitude of the Gaussian function used for correction is even and isotropic regardless of the location, and σX=σY. The magnitude of σX is set equal to the dimension in the Y direction of the uppermost cyst. No offset is added to the distribution. In this case, the intensity is corrected, but the image depicts that the four cysts vary in intensity. That is, the corrected intensity decreases in the positive direction on the X axis. This is because the intensity is corrected without taking the resolution into account, resulting in improper correction.

FIG. 3C depicts that the intensity is corrected using the technique according to Embodiment 1. The magnitude of the Gaussian function used for correction is varied near each of the four cysts. The magnitudes of σX and σY are set equal to the dimensions of the cyst in the corresponding directions. No offset is added to the distribution as in FIG. 3B. In this case, the image depicts that the intensities of the four cysts are corrected and are even.

In Embodiment 1, the Gaussian function used by the intensity correction processor 21 varies between both the X and Y directions and the Z direction. However, the present invention is not limited to this configuration. The magnitude, in the Z direction, of the Gaussian function used may vary in the Z direction on account of the resolution, or the magnitudes of the Gaussian function in the X, Y, and Z directions may or may not vary depending on the location.

Embodiment 1 adopts the apparatus 100 based on one-directional laser irradiation. However, for the present technique, as long as data acquired by the object information acquiring apparatus involve changes in resolution attributed to the apparatus, the technique according to Embodiment 1 is applicable even with a change in the configuration of the apparatus 100. That is, the present technique is also applicable to various laser irradiation schemes, a bowl-like arrangement of probes 17, planar and non-planar scan schemes, and a handheld photoacoustic diagnosis apparatus.

In the present embodiment, the resolution information relative to the certain point is used as the variance value for the Gaussian function. However, resolution information relative to the position in the object 15 for the apparatus 100 may be used as the variance value for the Gaussian function.

As described above, the present embodiment can make the intensity of the object information even with a variation in resolution attributed to the apparatus. As a result, images based on object information with visually even brightness can be displayed.

Embodiment 2

Figure 4:
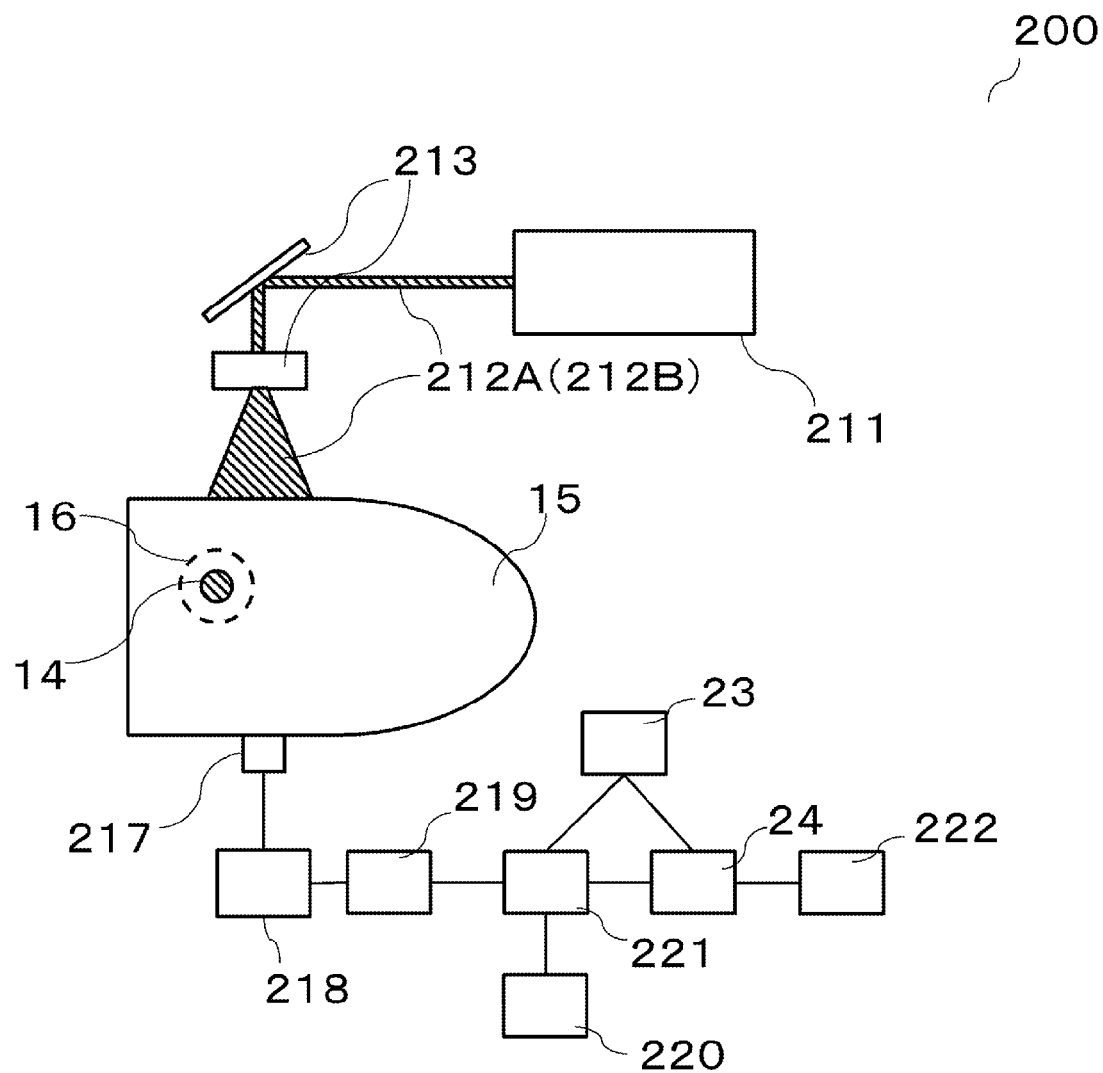
FIG. 4 is a block diagram depicting Embodiment 2 of an object information acquiring apparatus according to the present invention.

FIG. 4 is a block diagram depicting Embodiment 2 of the object information acquiring apparatus according to the present invention. Components of Embodiment 2 identical to those in Embodiment 1 are denoted by the same reference numerals and will thus not be described below. Furthermore, components of Embodiment 2 similar to the corresponding components in Embodiment 1 are denoted by numbers in the 200s which are the same in tens place and in ones place as the numbers in Embodiment 1. Description of these components is omitted as long as the description is not needed. However, regardless of this, numbers in the 200s are used for the whole object information acquiring apparatus.

In this regard, Embodiment 1 uses resolution information relative to a certain point as the variance value for the Gaussian function. However, Embodiment 2 uses resolution information relative to a position in an object 15 of an object information acquiring apparatus 200 (hereinafter referred to as an "apparatus 200"). The "resolution information relative to the position in the object 15" assumes analytically calculated resolution information such as voxels inside a measured distribution of absorption coefficients. This is a difference from the "resolution information relative to a certain information" in Embodiment 1. Furthermore, the intensity is corrected so as to avoid varying the relative ratio of absorption coefficient values between the distributions of absorption coefficients for multiple wavelengths to keep an oxygen saturation value calculated from the distributions of absorption coefficients unchanged after the correction. In the present embodiment, the distribution of object information is voxel data in the distribution of three-dimensional absorption coefficients. The resolution information is the distribution of three-dimensional resolution information.

The oxygen saturation is function information that can be calculated by comparing the distributions of absorption coefficients created by light sources with different wavelengths. The function information as used herein is information obtained by photoacoustic spectroscopy (photoacoustic imaging) and is, for example, information on the concentrations of particular substances in the object such as glucose and hemoglobin. It is assumed that, when the molar absorption coefficient of the blood is measured using light with a wavelength $\lambda_1$ and a wavelength $\lambda_2$, light absorption is negligibly low at the wavelength $\lambda_1$ and the wavelength $\lambda_2$ except for hemoglobin. Based on this assumption, molar absorption coefficients $\mu_a(\lambda_1)$ [mm$^{-1}$] and $\mu_a(\lambda_2)$ [mm$^{-1}$] calculated using the wavelength $\lambda^1$ and the wavelength $\lambda^2$ are expressed by:

[Math. 6]

$$\mu_a(\lambda_1) = \epsilon_{ox}(\lambda_1)C_{ox} + \epsilon_{de}(\lambda_1)C_{de} \qquad \text{Equation 6}$$

[Math. 7]

$$\mu_a(\lambda_2) = \epsilon_{ox}(\lambda_2)C_{ox} + \epsilon_{de}(\lambda_2)C_{de} \qquad \text{Equation 7}$$

In Equations 6 and 7, the amounts (mol) of oxygenated hemoglobin and reduced hemoglobin are denoted by $C_{ox}$ and $C_{de}$, and molar absorption coefficients [mm$^{-1}$mol$^{-1}$] for oxygenated hemoglobin and reduced hemoglobin at a wavelength $\lambda$ are denoted by $\epsilon_{ox}(\lambda)$ and $\epsilon_{de}(\lambda)$. The values $\epsilon_{ox}(\lambda)$ and $\epsilon_{de}(\lambda)$ are obtained by pre-measurement or from documents. Simultaneous equations in Equations 6 and 7 are solved using measured values $\mu_a(\lambda_1)$ and $\mu_a(\lambda_2)$ to obtain $C_{ox}$ and $C_{de}$. When a large number of wavelengths are used, the number of equations increases consistently with the number of wavelengths. Thus, $C_{ox}$ and $C_{de}$ are obtained using the least-square method. The oxygen saturation is defined by the rate of oxygenated hemoglobin in the whole hemoglobin in Equation 8 and can be calculated as in Equation 5. Consequently, the oxygen saturation can be obtained.

[Math. 8]

$$SO_2 = \frac{C_{ox}}{C_{ox} + C_{de}} \qquad \text{Equation 8}$$

In the present embodiment, the rate of the correction, at one wavelength, of the distribution of absorption coefficients that is the distribution of object information is multiplied by the distributions of absorption coefficients for other wavelengths. Based on the result of the multiplication, the intensity of each distribution of absorption coefficients can be corrected without a change in the ratio of the intensity of the absorption coefficient among a plurality of wavelengths. Thus, the relative ratio of the absorption coefficient intensity is prevented from being changed to avoid changing, after the correction, a function information value that is object information such as the oxygen saturation which is determined by a comparative operation of the relative ratio.

Furthermore, in the present embodiment, the abundance ratio of hemoglobin, that is, the oxygen saturation, has been described. However, the object information acquiring apparatus 200 can, as far as characteristic absorption spectrums are exhibited, use a similar principle to calculate the distribution of concentration information that is the abundance ratio of a substance other than hemoglobin such as fat, melanin, moisture or the mammary gland tissue.

(Basic Configuration)

The apparatus 200 according to Embodiment 2 is different from the apparatus according to Embodiment 1 in that a light source 211 delivers pulsed laser light at multiple lengths and in that an intensity correction processor 221 calculates a correction ratio. The apparatus 200 according to Embodiment 2 is further different from the apparatus according to Embodiment 1 in that the apparatus 200 has a memory 23 that calculates and holds the relative ratio of the absorption coefficient value based on the correction process and a function information acquiring unit 24 that calculates object function information that is object information such as the oxygen saturation.

<<Intensity Correction Processing Section 221>>

The intensity correction processor 221 executes an intensity correction process on a first distribution of absorption coefficients obtained by application of pulsed laser light 212A at a first wavelength. Then, an intensity correction rate is calculated which is needed to execute an intensity correction process on a second distribution of absorption coefficients obtained by application of pulsed laser light 212A at a second wavelength. The intensity correction rate is data resulting from division of the first distribution of absorption coefficients already objected to the intensity correction process by the first distribution of absorption coefficients not objected to the intensity correction process yet. The intensity correction rate is also three-dimensional voxel data with the same magnitude as that of the first distribution of absorption coefficients. These calculations are executed, and the distribution of absorption coefficients and the intensity correction rate for the first wavelength are held in the memory 23.

Moreover, the second distribution of absorption coefficients obtained by application of the pulsed laser light 212B at the second wavelength is multiplied by the intensity correction rate for the first wavelength to allow calculation of a corrected distribution of absorption coefficients at the second wavelength. The corrected second distribution of absorption coefficients at the second wavelength is transmitted to the function information acquiring unit 24. The embodiment for the two wavelengths has been described, but the intensity correction may be performed on distributions of absorption coefficients at three or more wavelengths. In that case, corrected distributions of absorption coefficients at a plurality of wavelengths can be generated by applying an intensity correction rate for a first wavelength to distributions of absorption coefficients at other plurality of wavelengths.

In the present embodiment, a method for intensity correction for a first distribution of absorption coefficients is executed as follows. First, the first distribution of absorption coefficients is blurred using a convolution kernel to calculate an intensity trend distribution, and an offset is added to the intensity trend distribution. Subsequently, the original first distribution of absorption coefficients is divided by the first distribution of absorption coefficients with the offset addition. Thus, the intensity of the first distribution of absorption coefficients has been corrected.

A difference from Embodiment 1 is that a three-dimensional distribution of resolution information is used as resolution information. The three-dimensional distribution of absorption coefficients is obtained by performing simulation on each of the voxels in voxel data to calculate, for each voxel, resolution information on the apparatus for each direction. The resolution information obtained is used to generate a convolution kernel for each voxel. The convolution sum of the convolution kernels corresponding to the voxels in the distribution of absorption coefficients is determined. Then, based on the convolution sum, the intensity trend distribution of the first distribution of absorption coefficients can be calculated.

<<Data Holding Section 23>>

The memory 23 serves to hold the corrected distribution of absorption coefficients at the first wavelength and the intensity correction rate for the first wavelength calculated by the intensity correction processor 221 and to transmit these pieces of information to the function information acquiring unit 24 in accordance with a request from the function information acquiring unit 24. In this case, the corrected distribution of absorption coefficients at the first wavelength is held, but of course, distributions of absorption coefficients at a plurality of wavelengths, corrected distributions of absorption coefficients at a plurality of wavelengths, and intensity correction rates for a plurality of wavelengths may be held.

<<Functional-Information Acquisition Section 24>>

The function information acquiring unit 24 calculates function information from corrected distributions of absorption coefficients at a plurality of wavelengths. In the present embodiment, the oxygen saturation of the blood can be calculated by performing a comparative operation between a corrected distribution of absorption coefficients at a first wavelength and a corrected distribution of absorption coefficients at a second wavelength in accordance with Equation 3, Equation 4, and Equation 5. The oxygen saturation can also be obtained in the form of three-dimensional voxel data with the same magnitude as that of the distribution of absorption coefficients.

Flow of the Process According to Embodiment 2

Figure 5A:
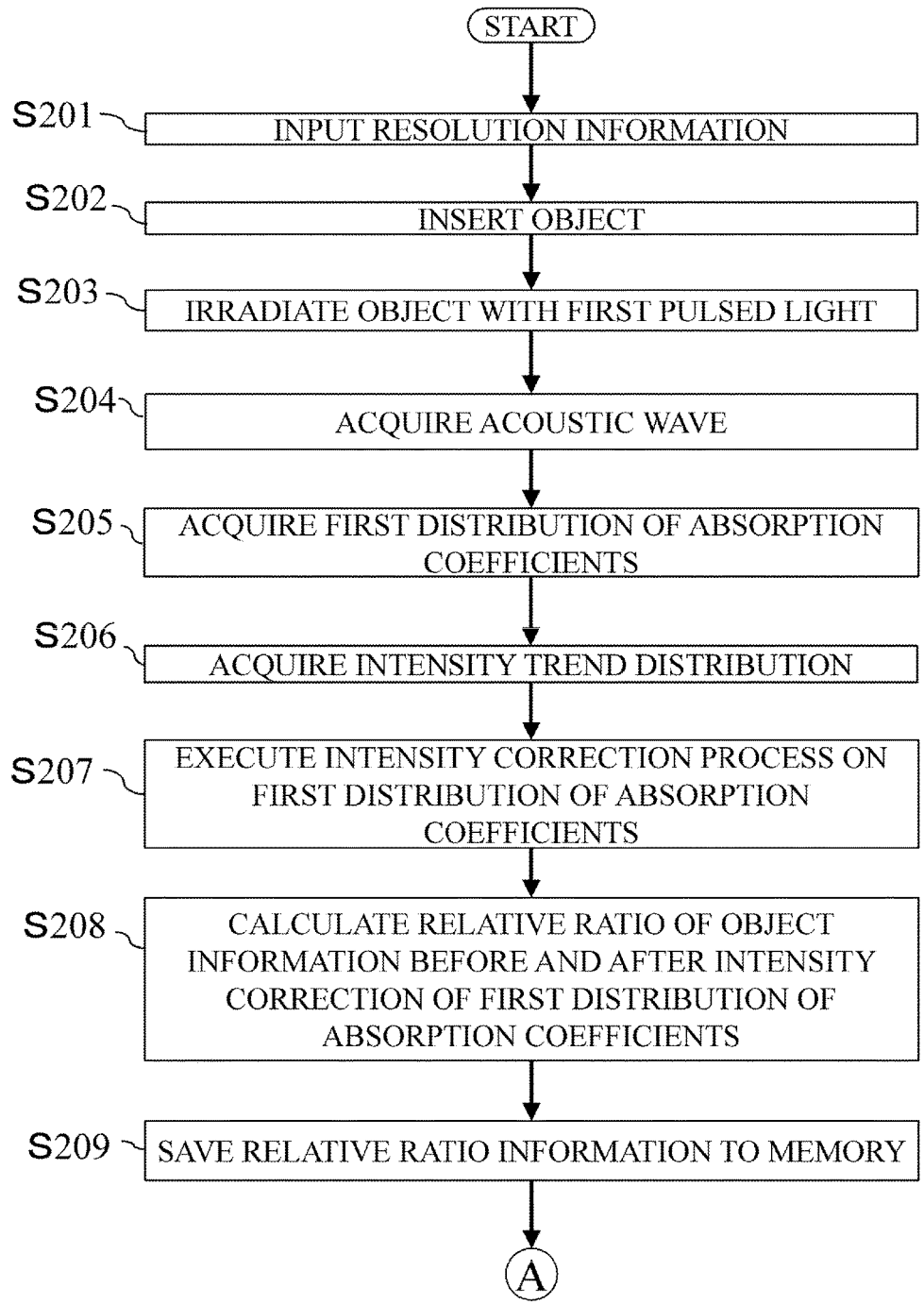
FIG. 5A is a flowchart depicting functions of the object information acquiring apparatus according to Embodiment 2.

FIG. 5A is a flowchart depicting a process executed by the apparatus 200 according to Embodiment 2. First, in simulation, resolution information on each of the voxels in the data in the apparatus 200 for each direction is calculated, an offset is pre-inputted to the apparatus 200, and then the process starts. In step S201, the resolution information, in this case, a three-dimensional distribution of absorption coefficients, is held in the apparatus 200. In step S202, the breast, which is a living body, is inserted into the apparatus 200 as the object 15. The object 15 is irradiated with pulsed laser light 212A at a first wavelength of 756 nm. In step S204, photoacoustic measurement is started.

In step S205, a signal processor 218 and a data processor 219 perform arithmetic operations on an acoustic wave acquired based on the pulsed laser light 212A to calculate the distribution of absorption coefficients at the first wavelength for the object. In step S206, the first distribution of absorption coefficients is blurred using a convolution kernel generated in each voxel in accordance with the input resolution information, and an offset is added to the resultant distribution of absorption coefficients to obtain an intensity correction rate. In step S207, the original distribution of absorption coefficients is divided by the resultant intensity trend distribution to correct the distribution of absorption coefficients at the first wavelength. In step S208, the corrected distribution of absorption coefficients at the first wavelength is divided by the original distribution of absorption coefficients at the first wavelength to obtain an intensity correction rate that is a rate changed as a result of the correction. In step S209, the intensity correction rate is saved to the memory.

Figure 5B:
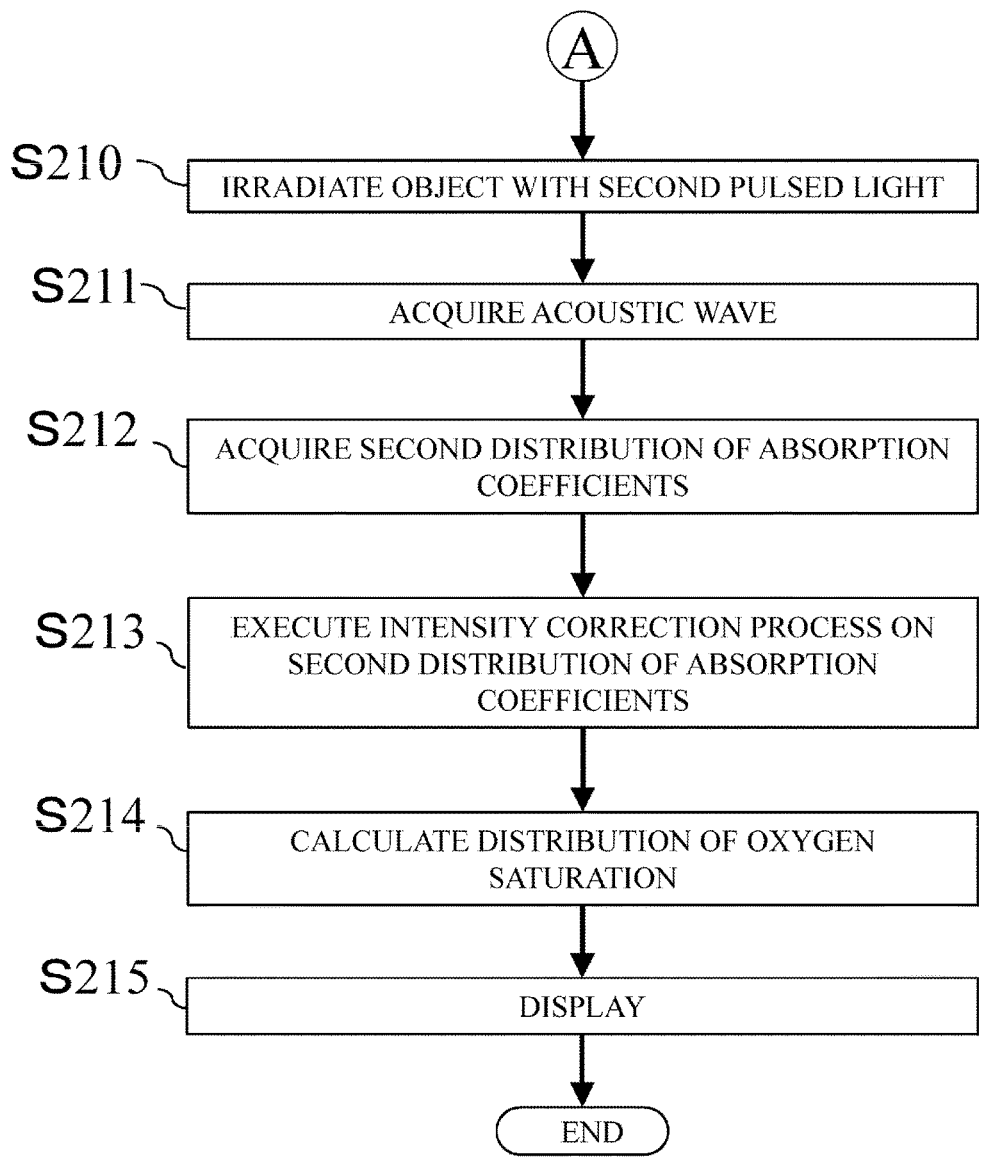
FIG. 5B is a flowchart depicting functions of the object information acquiring apparatus according to Embodiment 2.

FIG. 5B is a flowchart depicting a process executed by the apparatus 200 according to Embodiment 2. In step S210 after the step S209, the object is irradiated with pulsed laser light 212B of 797 nm that is a second wavelength. In step S211, photoacoustic measurement is started. In step S212, the signal processor 218 and the data processor 219 perform arithmetic operations on an acoustic wave acquired based on the pulsed laser light 212B to calculate a second distribution of absorption coefficients at the second wavelength for the object 15.

In step S213, an intensity correction process is executed on the second distribution of absorption coefficients obtained (S5). The intensity correction process in this case is executed by multiplying the distribution of absorption coefficients at the second wavelength by the intensity correction rate calculated for the first wavelength. In step S214, a comparative operation is performed between the distribution of absorption coefficients at the first wavelength with the intensity corrected and the distribution of absorption coefficients at the second wavelength with the intensity corrected to calculate the oxygen saturation. In step S215, the oxygen saturation is calculated.

As described above, in Embodiment 2, the relative ratio of the distribution of absorption coefficients is maintained in spite of the correction of the distribution, allowing the oxygen saturation value to be calculated.

As described above, in the present embodiment, one of the absorption coefficients is used to allow the intensity of the other absorption coefficient to be easily corrected. This enables a reduction in time for processing executed by the apparatus in acquiring function information such as the oxygen saturation. Furthermore, the relative ratio of the distribution of absorption coefficients is maintained in spite of the correction of the intensity of the distribution, allowing the oxygen saturation to be calculated.

Embodiment 3

Figure 6:
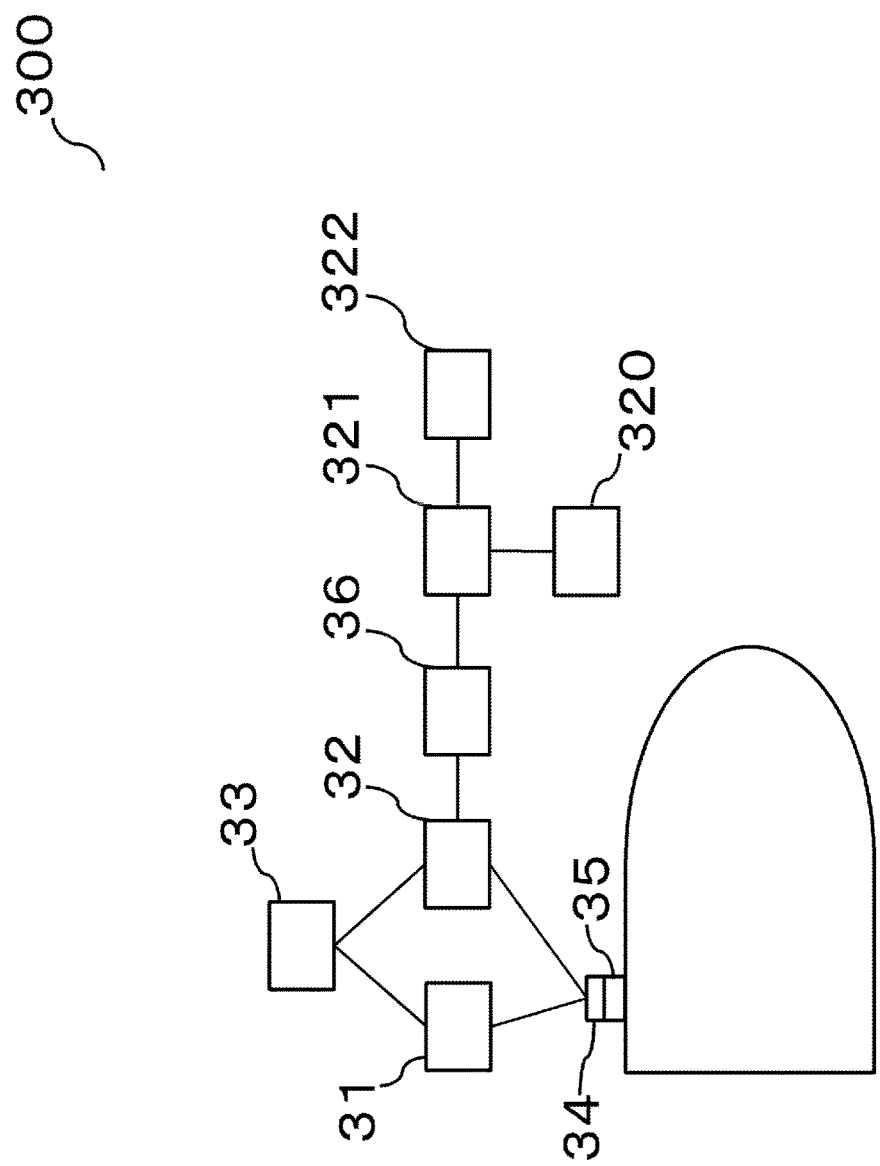
FIG. 6 is a block diagram depicting Embodiment 3 of an object information acquiring apparatus according to the present invention.

FIG. 6 is a block diagram depicting Embodiment 3 of an object information acquiring apparatus according to the present invention. Components of Embodiment 2 similar to the corresponding components in Embodiment 1 in FIG. 1 are denoted by numbers in the 300s which are the same in tens place and in ones place as the numbers in Embodiment 1. Description of these components is omitted as long as the description is not needed. However, regardless of this, numbers in the 300s are used for the whole object information acquiring apparatus. A object information acquiring apparatus 300 in Embodiment 3 (hereinafter referred to as an "apparatus 300") is, for example, a three-dimensional ultrasonic diagnosis apparatus that performs intensity correction on the distribution of object information according to Embodiment 3.

In the object information acquiring apparatus 300, a three-dimensional ultrasonic tomographic image that is a measured distribution of object information may suffer intensity unevenness due to a factor specific to the apparatus such as the directionality of a probe including an ultrasonic probe 34 and a plurality of conversion elements 35. In contrast, in Embodiment 3, the intensity unevenness of the three-dimensional ultrasonic tomographic image is corrected taking into account a difference in the resolution in each direction depending on the location of the apparatus 300.

(Basic Configuration)

The ultrasonic diagnosis apparatus according to the Embodiment 3 has a transmission circuit 31, a reception circuit processor 32, a system controller 33, a resolution information acquiring unit 320, an intensity correction processor 321, and a display 322. The components from the transmission circuit 31 to the data processor 36 provide a distribution acquiring unit. The ultrasonic probe 34 transmits an ultrasonic wave and receives an acoustic wave having propagated based on the transmission of the ultrasonic wave. That is, the ultrasonic probe 34 serves as a receiver that receives the acoustic wave having propagated and a transmitter that transmits the ultrasonic wave. The present invention is not limited to this configuration, and the transmitter and the receiver may be separately provided. Moreover, the ultrasonic probe 34 has a plurality of conversion elements 35 (also referred to as transducers). The resolution information acquiring unit 320, the intensity correction processor 321, and the display 322 are similar to the corresponding components in Embodiment 1 and Embodiment 2, and differences will be described below.

<<Transmission Circuit Processing Section 31>>

The transmission circuit 31 determines elements for transmission and associated delay times, based on setting information from the system controller 33. Then, the transmission circuit 31 transmits an electric signal that allows the ultrasonic probe 34 to be driven. The electric signal is converted into displacement signals by the conversion elements 35 in the ultrasonic probe 34. The displacement signals propagate toward the object 15 as ultrasonic waves.

<<Reception Circuit Processing Section 32>>

The reception circuit processor 32 determines delay times for receive signals based on depth information in received data, and executes a delay process on each receive signal. Thus, processing is executed to match the phases of signals resulting from ultrasonic echoes from the object which are received by the conversion elements 35.

<<System Control Section 33>>

The system controller 33 is a unit that controls the transmission circuit 31, the reception circuit processor 32, the ultrasonic probe 34, and the data processor 36.

<<Ultrasonic Probe 34>>

The ultrasonic probe 34 transmits and receives ultrasonic waves.

<<Conversion Elements 35>>

The conversion elements 35 are a unit that receives ultrasonic echoes resulting from the reflection or scattering, by the object, of ultrasonic waves having propagated after transmission and which converts the ultrasonic echoes into electric signals. The conversion elements 35 may be a single acoustic detector or a plurality of acoustic detectors. Furthermore, the conversion elements 35 may be a plurality of reception elements arranged one- or two-dimensionally. The use of multidimensional array elements allows an acoustic wave to be simultaneously received at a plurality of locations, enabling a reduction in measurement time and also in adverse effects such as vibration of the object.

The conversion elements 35 desirably have a high sensitivity and a wide frequency band. Specifically, the conversion elements 35 use piezoelectric ceramics (PZT), polyvinylidene defluoride (PVDF), capacitive micromachine ultrasonic transducers (CMUT), or Fabry-Perot interferometers. However, any conversion elements may be used without limitation as long as the conversion elements provide the functions of a probe.

<<Data Processing Section 36>>

The data processor 36 is a unit that images electric signals objected to the delay process by the reception circuit processor 32. A process such as LOG compression is executed on the signals objected to the delay process by the reception circuit processor 32 to create a three-dimensional ultrasonic tomographic image.

Flow of the Process According to Embodiment 3

Figure 7:
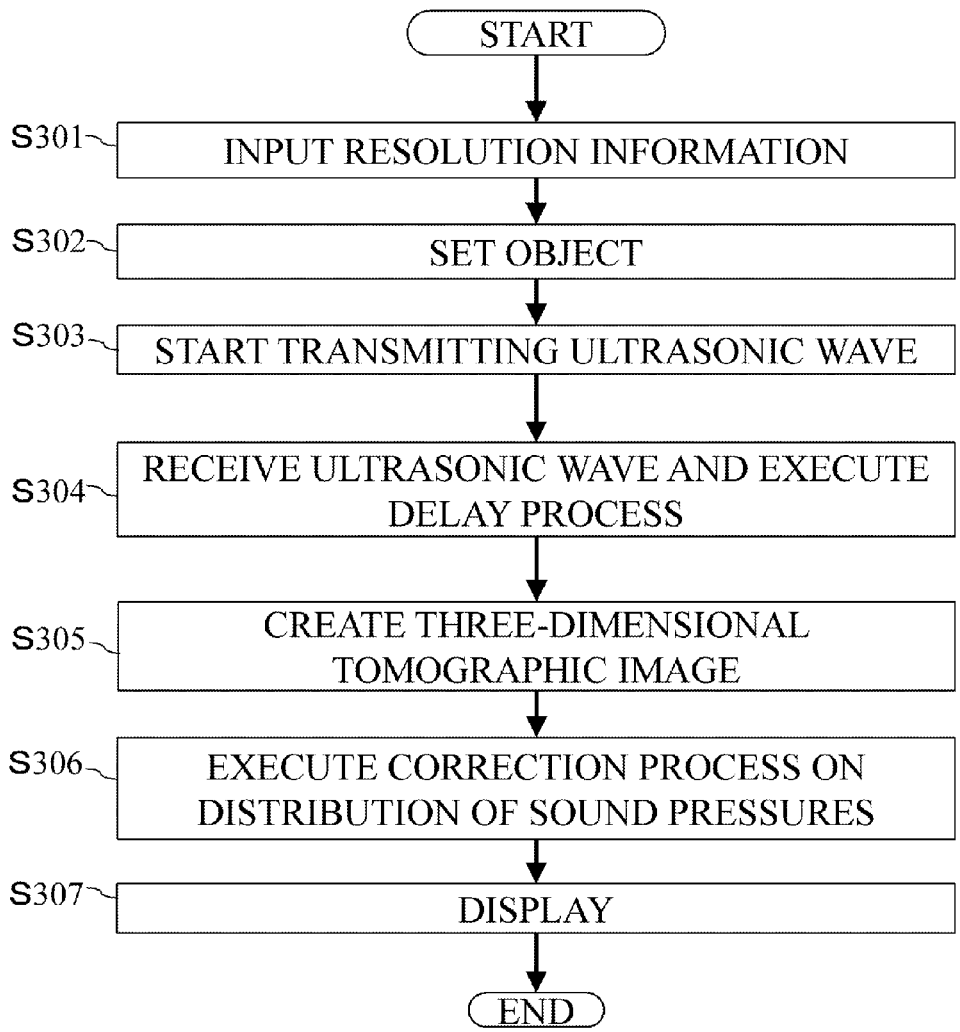
FIG. 7 is a flowchart depicting functions of the object information acquiring apparatus according to Embodiment 3.

FIG. 7 is a flowchart depicting a process executed by an ultrasonic diagnosis apparatus that is an apparatus 300 according to Embodiment 3 of the present invention.

As is the case with Embodiment 1, a phantom or the like is pre-measured, resolution information on a three-dimensional ultrasonic tomographic image measured by the apparatus 300 is calculated for each location, and then the flow starts. In step S301, the distribution of resolution information including pieces of resolution information is input to the apparatus. In step S302, the breast, which is a living body, is set in the apparatus 300 as the object 15. In step S303, ultrasonic measurement is started. First, a position to which an ultrasonic wave is to be transmitted is determined. The system controller 33 transmits setting information to the transmission circuit 31. Based on the setting information, the transmission circuit 31 determines elements for transmission and associated delay times. The transmission circuit 31 then transmits electric signals that allow corresponding elements 35 in the ultrasonic probe 34 to be driven. The electric signals are converted into displacement signals by the conversion elements 35, and the displacement signals propagate toward the object 15 as ultrasonic waves.

In step S304, the ultrasonic waves thus having propagated after transmission are reflected or scattered by the object and return to the conversion elements 35 as ultrasonic echoes. A plurality of conversion elements 35 forming a reception aperture convert the ultrasonic echoes into electric signals. Thus, biological information on the object 15 can be acquired in the form of receive signals. The receive signals are transmitted to the reception circuit processor 32. The reception circuit processor 32 determines delay times for reception times based on depth information in receive data and executes a delay process on each receive signal.

In step S305, the signal objected to the delay signal is transmitted to the data processor 36, where a process such as LOG compression is executed on the signal to create three-dimensional ultrasonic tomographic image data. In step S306, the calculated three-dimensional ultrasonic tomographic image data are corrected. The input distribution of resolution information is used to calculate a convolution kernel. A convolution of the kernel and the three-dimensional ultrasonic tomographic image is performed. An offset is added to the convoluted three-dimensional ultrasonic tomographic image to obtain an intensity trend distribution corresponding to a converted three-dimensional ultrasonic tomographic image. The original three-dimensional ultrasonic tomographic image is divided by the resultant converted three-dimensional ultrasonic tomographic image to correct the intensity unevenness of the converted three-dimensional ultrasonic tomographic image. In step S307, the corrected three-dimensional tomographic image is displayed.

According to Embodiment 3, the apparatus 300 can correct a fluctuation in the intensity of the calculated distribution of sound pressure intensities which is specific to the apparatus 300 to generate an ultrasonic image that has visually even brightness.

The technique in Embodiment 3 is adapted for the three-dimensional ultrasonic diagnosis apparatus that is the object information acquiring apparatus 300. However, the technique is widely applicable to ultrasonic diagnosis apparatuses in which the resolution of a created image varies depending on the position, such an ultrasonic diagnosis apparatus that generates two-dimensional images and a handheld ultrasonic diagnosis apparatus. For the handheld ultrasonic diagnosis apparatus, resolution information relative to each imaged location is calculated, the resolution information is used to calculate a convolution kernel, and the intensity unevenness of the two-dimensional ultrasonic image can be similarly corrected.

Embodiment 4

Figure 8:
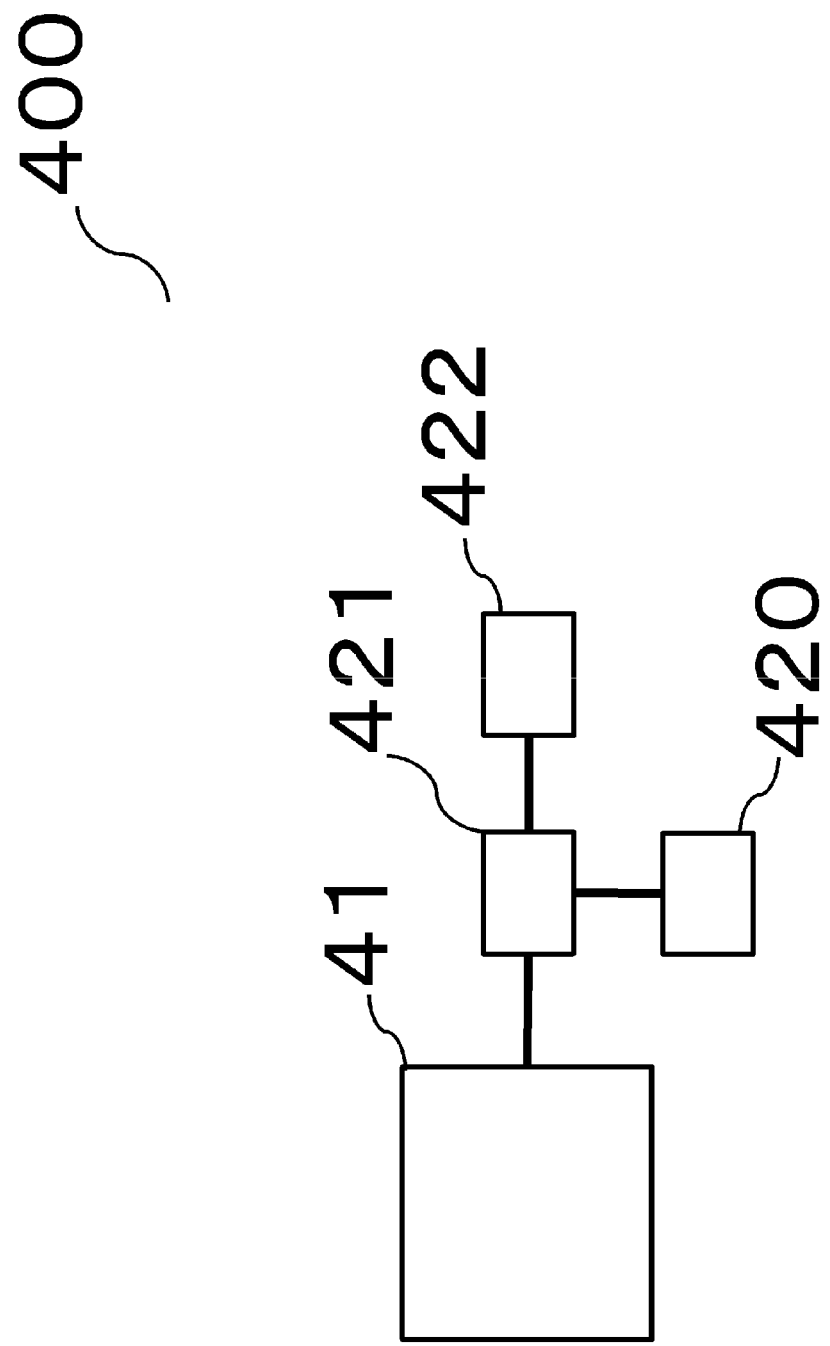
FIG. 8 is a block diagram depicting Embodiment 4 of an object information acquiring apparatus according to the present invention.

FIG. 8 is a block diagram depicting Embodiment 4 of an object information acquiring apparatus according to the present invention. Components of Embodiment 4 similar to the corresponding components in Embodiment 1 in FIG. 1 are denoted by numbers in the 400s which are the same in tens place and in ones place as the numbers in Embodiment 1. Description of these components is omitted as long as the description is not needed. However, regardless of this, numbers in the 400s are used for the whole object information acquiring apparatus.

Intensity correction is performed on the distribution of object information in a magnetic resonance imaging (MRI) apparatus that is an object information acquiring apparatus 400 according to Embodiment 4 (hereinafter referred to as an "apparatus 400"). In magnetic resonance imaging apparatus, the intensity unevenness (sensitivity unevenness) of the measured distribution of object information may occur due to the sensitivity distribution of a detector, the shape of a measured object, the unevenness of magnetic fields, the dielectric effect of RF pulses, or unevenness caused by a stationary wave effect. In contrast, the apparatus 400 corrects the intensity unevenness of the distribution of object information taking a difference in spatial resolution depending on the location.

(Basic Configuration)

The apparatus 400 according to Embodiment 4 has a magnetic resonance imaging unit 41 that acquires object information, a resolution information acquiring unit 20, an intensity correction processor 21, and a display 22.

Flow of the Process According to Embodiment 4

Figure 9:
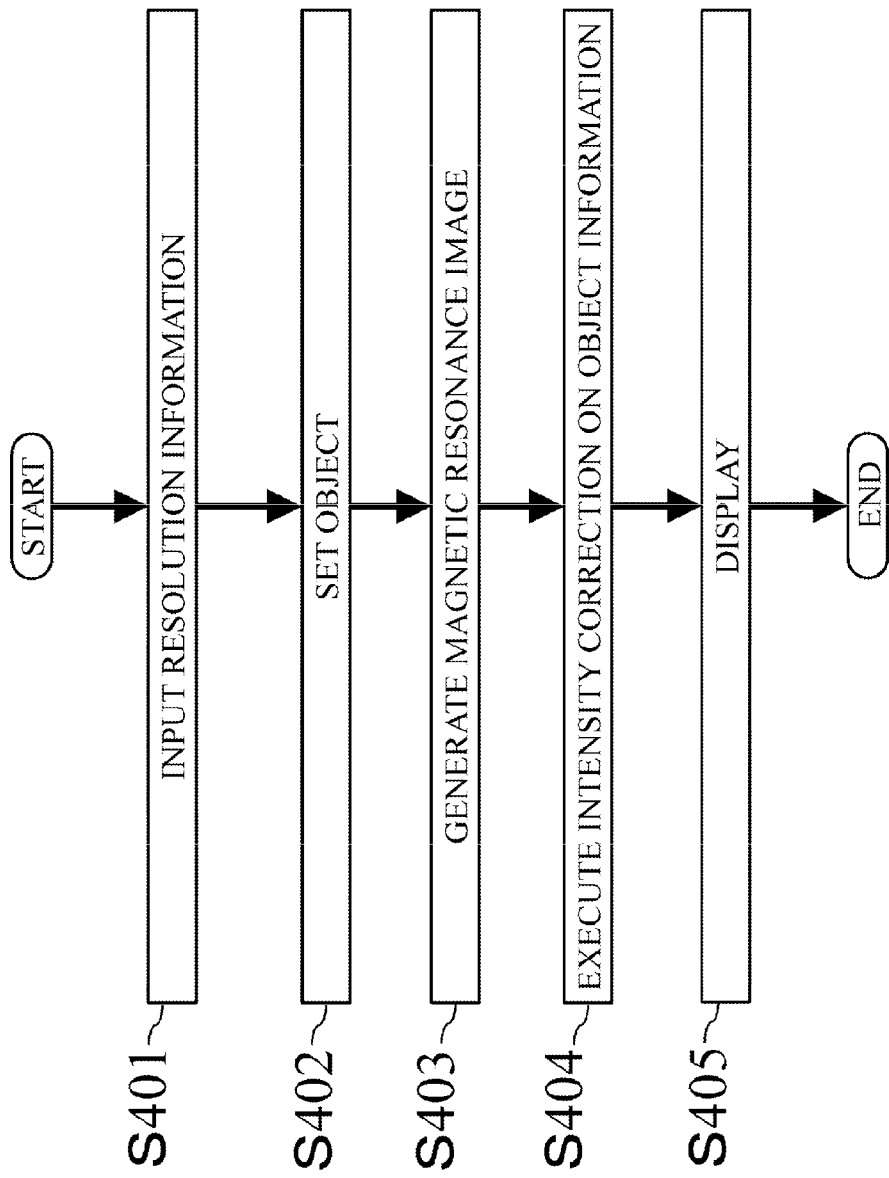
FIG. 9 is a flowchart depicting functions of the object information acquiring apparatus according to Embodiment 4.
Figure 10:
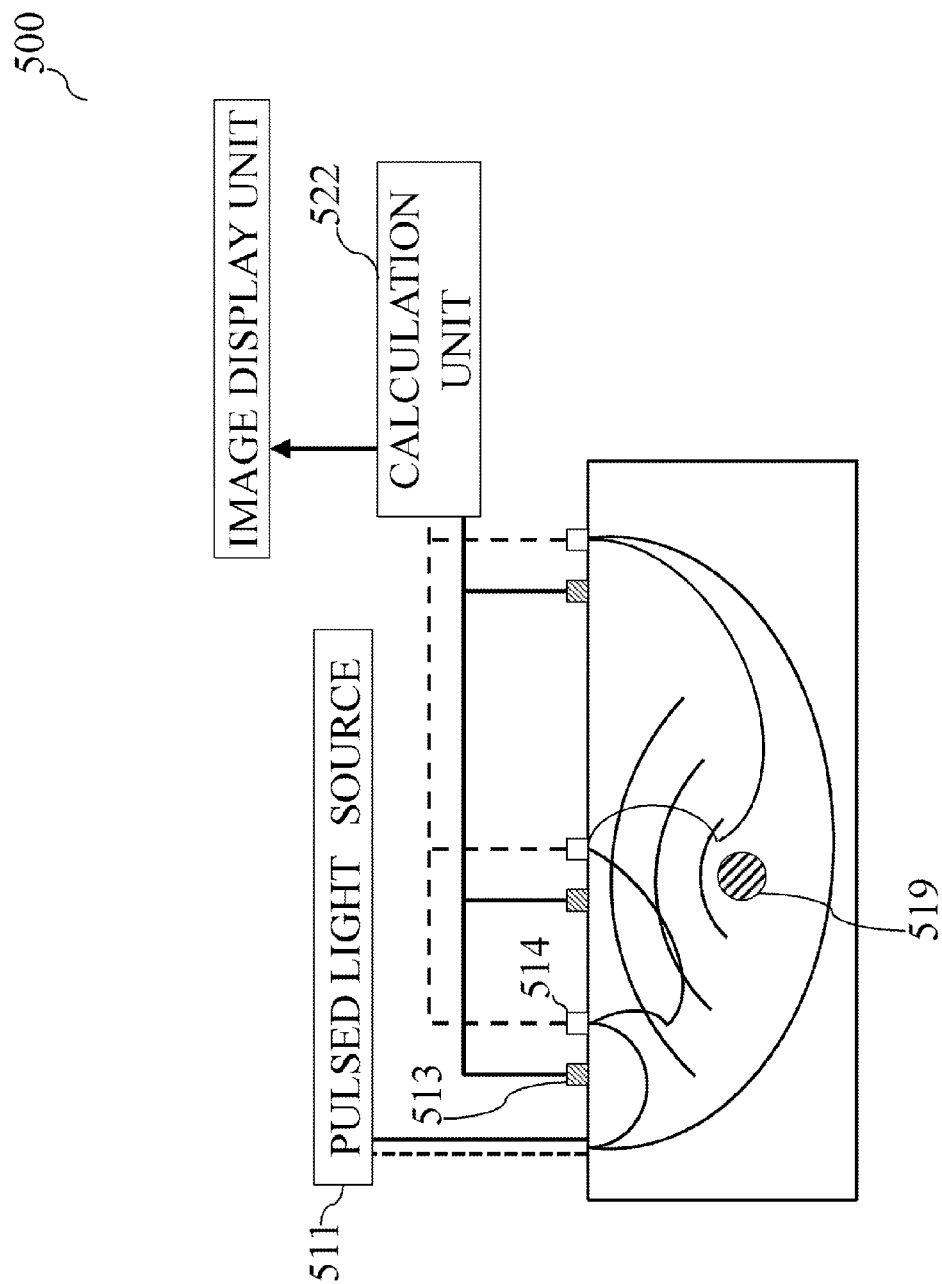
FIG. 10 is a diagram depicting an example of a related art.

FIG. 9 is a flowchart depicting a process executed by the apparatus 400 according to Embodiment 4 of the present invention. A phantom is pre-measured, discrete spatial resolution information is interpolated to calculate the spatial resolution of the data measured by the apparatus, for each location, and the flow starts. In step S401, spatial resolution distribution information including calculated spatial resolutions is input to the apparatus. In step S402, the breast, which is the object 15, is set in the apparatus 400. In step S403, magnetic resonance imaging is started to generate an image.

In step S404, for the image generated, the intensity of object information is corrected in accordance with the spatial resolution distribution information. A method for correcting the intensity involves calculating a convolution kernel in accordance with the input spatial resolution distribution information and performing a convolution of the kernel and the distribution of object information. An offset is added to the convoluted distribution of object information to obtain an intensity trend distribution. The original distribution of object information is divided by the resultant intensity trend distribution to correct the object information. In step S405, the corrected object information is displayed.

Embodiment 4 enables configuration of the apparatus 400 that corrects a fluctuation in the intensity of the calculated distribution of object information which is specific to the apparatus to provide visually even brightness.

An arithmetic device in a computer can execute signal processing described above in the embodiments and activation control for the apparatus by reading corresponding programs saved in a memory in the computer.

The arithmetic device typically includes an element such as a CPU, a GPU, or an A/D converter or a circuit such as an FPGA or an ASIC. The arithmetic device may be a single element or a single circuit or may include a plurality of elements or a plurality of circuits. Furthermore, each process executed by the arithmetic device may be executed by any element or circuit. The arithmetic device may include the signal processor, the data processor, the resolution information acquiring unit, the intensity correction processor, the function information acquiring unit, the transmission circuit, the reception circuit processor, and the system controller.

Furthermore, the memory typically includes a storage medium such as ROM, RAM, or a hard disk. The storage medium to which programs are saved is a non-transitory recording medium. Additionally, the memory may be a single storage medium or may include a plurality of storage media. The memory may include the memory.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment (s) of the present invention, and by a method performed by the computer of the system or apparatus by, for example, reading out and executing the computer executable instructions from the storage medium to perform the functions of one or more of the above-described embodiment (s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-046388, filed on Mar. 10, 2014, which is hereby incorporated by reference herein in its entirety.

What is claimed is:

1. An object information acquiring apparatus comprising:
an object information acquiring unit configured to acquire object information at each of a plurality of positions in an object based on a received acoustic wave propagating from the object;
a resolution information acquiring unit configured to acquire resolution information of the object information at each of the plurality of positions; and
an intensity correction processor configured to correct an intensity of the object information at each of the plurality of positions in the object on the basis of a distribution of the resolution information.

2. The object information acquiring apparatus according to claim 1, wherein the intensity correction processor acquires an intensity trend at each of the plurality of positions in the object by blurring the object information at each of the plurality of positions on the basis of the resolution information at each of the plurality of positions and corrects the intensity at each of the plurality of positions on the basis of the intensity trend at each of the plurality of positions and the object information at each of the plurality of positions.

3. The object information acquiring apparatus according to claim 2, wherein the intensity trend at each of the plurality of positions is acquired on the basis of a convolution of a convolution kernel acquired based on the resolution information at each of the plurality of positions, and the object information at each of the plurality of positions.

4. The object information acquiring apparatus according to claim 3, wherein the convolution kernel is a Gaussian kernel.

5. The object information acquiring apparatus according to claim 4, wherein the intensity correction processor divides the object information at each of the plurality of positions by the intensity trend at each of the plurality of positions to correct the intensity in the object information at each of the plurality of positions.

6. The object information acquiring apparatus according to claim 4, wherein the intensity correction processor divides the object information at each of the plurality of positions by the intensity trend at each of the plurality of positions with an offset added thereto to correct the intensity in the of object information at each of the plurality of positions.

7. The object information acquiring apparatus according to claim 1, further comprising a light irradiator configured to irradiate the object with light to allow the acoustic wave to propagate from the object.

8. The object information acquiring apparatus according to claim 7, wherein
the light irradiator irradiates the object with first light with a first wavelength and second light with a second wavelength, which is different from the first wavelength, to allow a first acoustic wave corresponding to the first light and a second acoustic wave corresponding to the second light to propagate from the object,
the object information acquiring unit acquires first object information at each of the plurality of positions on the basis of the first acoustic wave and acquires second object information at each of the plurality of positions on the basis of the second acoustic wave, and the intensity correction processor corrects the intensity of first object information included in the first object information at each of the plurality of positions, acquires an intensity correction rate on the basis of the corrected first object information at each of the plurality of positions and the first object information at each of the plurality of positions which is uncorrected, and corrects the intensity of a second object information included in the second distribution of object information at each of the plurality of positions on the basis of the second object information at each of the plurality of positions and the intensity correction rate.

9. The object information acquiring apparatus according to claim 8, further comprising a function information acquiring unit configured to acquire third object information at each of the plurality of positions on the basis of the corrected first and second object information at each of the plurality of positions.

10. The object information acquiring apparatus according to claim 9, wherein the first and second object information at each of the plurality of positions are absorption coefficients, and the third object information at each of the plurality of positions is oxygen saturation.

11. The object information acquiring apparatus according to claim 8, wherein the intensity correction processor multiplies the second object information at each of the plurality of positions by the intensity correction rate to correct the intensity of the second object information at each of the plurality of positions.

12. The object information acquiring apparatus according to claim 1, further comprising a transmitter configured to transmit an ultrasonic wave to the object to allow the acoustic wave to propagate.

13. The object information acquiring apparatus according to claim 1, further comprising a receiver configured to receive an acoustic wave propagating from the object,
wherein the receiver transmits an acoustic wave to the object to allow the acoustic wave to propagate and then receives the acoustic wave.

14. The object information acquiring apparatus according to claim 1, further comprising a display configured to display an image on the basis of the object information having the corrected intensity.

15. A signal processing method comprising:
acquiring resolution information of object information at each of a plurality of positions in an object; and
correcting an intensity of the object information at each of the plurality of positions in the object on the basis of a distribution of the resolution information.

16. A non-transitory computer readable storing medium recording a program allowing a computer to execute the signal processing method according to claim 15.

17. The object information acquiring apparatus according to claim 1, further comprising a receiver configured to receive an acoustic wave propagating from the object.

18. The object information acquiring apparatus according to claim 1, further comprising a receiver configured to receive an acoustic wave propagating from the object.

* * * * *